United States Patent [19]  [11] 3,959,262
Mathais et al.  [45] May 25, 1976

[54] METHOD FOR PREPARING AZINES

[75] Inventors: Henri Mathais, Foy-les-Lyon; Jean-Pierre Schirmann, Brignais; Pierre Tellier, Oullins; Francis Weiss, Pierre-Benite, all of France

[73] Assignee: Produits Chimiques Ugine Kuhlmann, Paris, France

[22] Filed: Sept. 20, 1972

[21] Appl. No.: 290,507

[30] Foreign Application Priority Data
Oct. 8, 1971  France .............................. 71.36311

[52] U.S. Cl. ..................... 260/240 G; 260/566 B
[51] Int. Cl.² ..................................... C07C 119/00
[58] Field of Search ................ 260/566 B, 240 G

[56] References Cited
UNITED STATES PATENTS
2,870,206  1/1959  Meyer et al. ................... 260/566 B Primary Examiner—Gerald A. Schwartz
Attorney, Agent, or Firm—Pennie & Edmonds

[57] ABSTRACT

A method is disclosed for preparing symmetrical azines of the formulas $$\begin{array}{c}R^1\\ \diagdown\\ R^2\end{array}C=N-N=C\begin{array}{c}R^1\\ \diagup\\ R^2\end{array} \quad (I)$$

$$\begin{array}{c}R^1\\ \diagdown\\ R^3\end{array}C=N-N=C\begin{array}{c}R^1\\ \diagup\\ R^3\end{array} \quad (II)$$

$$\begin{array}{c}R^3\\ \diagdown\\ R^4\end{array}C=N-N=C\begin{array}{c}R^3\\ \diagup\\ R^4\end{array} \quad (III)$$

and unsymmetrical azines of the formulas $$\begin{array}{c}R^1\\ \diagdown\\ R^2\end{array}C=N-N=C\begin{array}{c}R^1\\ \diagup\\ R^3\end{array} \quad (IV)$$

$$\begin{array}{c}R^1\\ \diagdown\\ R^2\end{array}C=N-N=C\begin{array}{c}R^3\\ \diagup\\ R^4\end{array} \quad (V)$$

and mixtures of azines (I), (II) and (IV) and (I), (III) and (V), wherein $R^1$, $R^2$, $R^3$ and $R^4$ each is a hydrogen atom, a straight chain alkyl radical of from 1 to 12 carbon atoms, a branched chain alkyl radical or unsubstituted or alkyl substituted cycloalkyl radical of from 3 to 12 carbon atoms, a hydrocarbon radical of from 6 to 12 carbon atoms containing a benzene ring; further provided that $R^1$ and $R^2$ can be the same or different radicals, $R^3$ is a radical different from $R^1$ and $R^2$ and $R^3$ and $R^4$ are radicals different from each other and each are different from $R^1$ and $R^2$; or $R^1$ and $R^2$ or $R^1$ and $R^3$ or $R^3$ and $R^4$ bonded to the same carbon atom together form an unsubstituted or aliphatic substituted alkylene radical of from 3 to 11 carbon atoms, each of the aforesaid radicals being unsubstituted or substituted with one or more radicals which are stable in the medium in which the azines are produced.

The method comprises reacting in the liquid phase, ammonia with a percarboxylic acid of the formula $$R^5-\underset{\underset{O}{\|}}{C}-O-OH \quad (VI)$$

wherein $R^5$ represents a hydrogen atom, a straight chain alkyl radical of from 1 to 18 carbon atoms, a branched chain alkyl radical or unsubstituted or alkyl substituted cycloalkyl radical of from 3 to 12 carbon atoms, a hydrocarbon radical of from 6 to 12 carbon atoms containing a benzene ring, further provided that the aforesaid radicals can contain a non-epoxidizable or epoxidizable ethylenic double bond and/or one or more radicals which are stable in the medium in which the azines are produced, in the presence of a carbonyl compound of the formula $$R^1-\underset{\underset{O}{\|}}{C}-R^2 \quad (VII)$$

alone or together with a different carbonyl compound $$R^1-\underset{\underset{O}{\|}}{C}-R^3 \quad (VIII)$$

$$R^3-\underset{\underset{O}{\|}}{C}-R^4 \quad (IX)$$

wherein $R^1$, $R^2$, $R^3$ and $R^4$ each have the same meaning defined above and recovering the azine or mixture of azines from the reaction medium.

5 Claims, No Drawings

METHOD FOR PREPARING AZINES

BACKGROUND OF THE INVENTION

I. Field of the Invention

This invention relates to a method for preparing symmetrical azines as well as mixtures containing symmetrical and unsymmetrical azines.

II. Description of the Prior Art

Aldehydes are known to react with ammonia in a complex manner giving rise to various addition, condensation or polymerization products (see for example, The Chemistry of the Carbon-Nitrogen Bond, S. Patai, Interscience, London, 1967, page 67) which can react with hydrogen peroxide to form unstable peroxide products.

Moreover, it is known that ammonia, an aldehyde or ketone, and hydrogen peroxide react together to produce aminoperoxides (J. Chem. Soc. 1969, C, page 2663) and in the presence of such catalysts as tungstic or molybdic acid, a mixture of cyclohexanone and ammonia is oxidized by hydrogen peroxide to form cyclohexanoneoxime (J. Gen. Chem. (U.S.S.R.) 1960, 30, 1635), or in the presence of the ammonium salts or hydroxides of metals of Group Ia and IIa of the Periodic Table of the Elements, result in azines (see copending application Ser. No. 267,921 filed June 30, 1972, now abandoned.

Another method for preparing azines comprises the oxidation of ammonia in the presence of a ketone or aldehyde by means of an oxidizing medium comprising hydrogen peroxide and cyanogen or a nitrile. This method is fully disclosed in commonly assigned pending U.S. application Ser. No. 152,413, filed June 11, 1971, now abandoned.

Still another method for preparing azines comprises oxidizing a secondary alcohol in the liquid phase to form peroxide products of the auto-oxidation of the alcohol and subsequently reacting the peroxidic products with ammonia in the presence of cyanogen or a nitrile. This method is fully disclosed in commonly assigned pending U.S. application Ser. No. 230,038, filed Feb. 28, 1972, now abandoned.

Percarboxylic acids are also known to react with N-substituted imines in an anhydrous medium to give oxaziridines (German patents 952,895 and 959,094).

SUMMARY OF THE INVENTION

It has been surprisingly discovered that symmetrical azines of the formulas

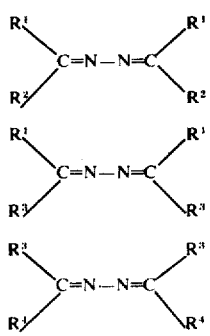

and unsymmetrical azines of the formulas

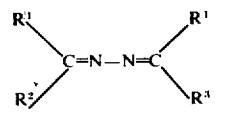

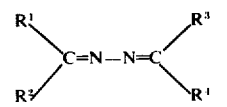

can be conveniently prepared in good yields by reacting in the liquid phase, ammonia with a percarboxylic acid of the formula

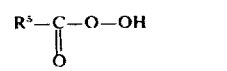

wherein $R^5$ represents a hydrogen atom, a straight chain alkyl radical of from 1 to 18 carbon atoms, a branched chain alkyl radical or unsubstituted or alkyl substituted cycloalkyl radical of from 3 to 12 carbon atoms, a hydrocarbon radical of from 6 to 12 carbon atoms containing a benzene ring, further provided that the aforesaid radicals can contain a non-epxoidizable or epoxidizable ethylenic double bond and/or one or more radicals which are stable in the medium in which the azines are produced, in the presence of a carbonyl compound of the formula wherein $R^1$, $R^2$, $R^3$ and $R^4$ each have the same meaning defined above.

When a single carbonyl compound (VII) is reacted according to the method of this invention, a symmetrical azine having the formula

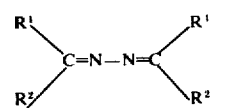

is produced.

When, for example, both $R^1$ and $R^2$ of carbonyl compound (VII) is hydrogen, the carbonyl compound is formaldehyde and the azine resulting from this method is the symmetrical aldazine, formaldazine, which has the formula

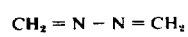

When only one of the substituents is hydrogen, the resulting aldazine, for example, has the formula

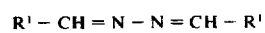

wherein the substituent $R^1$ is not hydrogen.

When neither of the substituents of the carbonyl compound (VII) is hydrogen, the carbonyl compound (VII) is a ketone and the resulting azine is a symmetrical ketazine of the formula

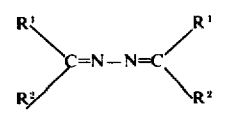

wherein none of the substituents $R^1$ and $R^2$ is hydrogen.

When in addition to carbonyl compound (VII), a different carbonyl compound (VIII) is simultaneously reacted according to the method of this invention, a mixture of symmetrical and unsymmetrical azines of the formulas

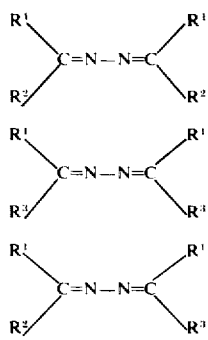

is produced.

And if in addition to carbonyl compound (VII), a different carbonyl compound (IX) is simultaneously reacted according to the method of this invention, a mixture of symmetrical and unsymmetrical azines of the formulas

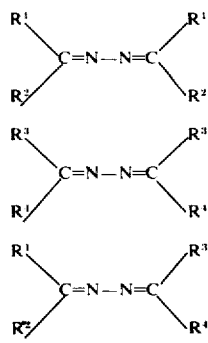

is produced.

When both carbonyl compounds (VII) and (VIII) or (VII) and (IX) are aldehydes, a mixture of symmetrical and unsymmetrical aldazines will be obtained. Similarly, if both carbonyl compounds (VII) and (VIII) or (VII) and (IX) are ketones, a mixture of symmetrical and unsymmetrical ketazines will be produced. And if one of the carbonyl compounds (VII), (VIII) or (IX) is an aldehyde and the other carbonyl compound which is being simultaneously reacted is a ketone, the method of this invention will yield a mixture of azines containing a symmetrical aldazine, a symmetrical ketazine and an unsymmetrical azine possessing the characteristics of both an aldazine and a ketazine.

Any number of different aldehydes and/or ketones may be reacted according to the method of this invention to yield mixtures of azines, the number of which are present in the mixture being made to depend upon the number of carbonyl compounds reacted.

DETAILED DESCRIPTION OF THE INVENTION

The percarboxylic acids (VI) useful in the process of this invention can possess a non-epoxidizable double bond or a readily epoxidizable double bond, notably in the position which is $\alpha,\beta$ with respect to the percarboxylic group and can contain such stable substituents as chlorine, bromine and fluorine atoms and nitro, hydroxy, alkoxy, carboxylic acid, carboxylic amide, i.e., carbamyl, carboxylic or ester and nitrile groups.

Some examples of percarboxylic acids conforming to formula (VI) which are advantageously employed in the process of this invention include those derived from such carboxylic acids as formic, acetic, propionic, butyric, isobutyric, valeric, isovaleric, pivalic, hexanoic, heptanoic, octanoic, $\alpha,\alpha'$-dimethyloctanoic, lauric, palmitic, stearic, hexahydrobenzoic, trifluoroperacetic, $\beta$-chloropropionic, $\beta$-methoxypropionic, $\beta$-hydroxycaproic and benzoic acid and its ortho, meta or para chloro, bromo, fluoro, methoxy, nitro or trifluoromethyl derivatives, and ortho, meta or para toluic, succinic, glutaric, adipic, crotonic, maleic, fumaric and phthalic acid.

The carbonyl compounds of this invention can contain substituents which are stable in the reaction medium such as chlorine, bromine, and fluorine atoms and nitro, hydroxy, alkoxy, carboxylic acid, carboxylic amide or ester and nitrile groups.

Some examples of aldehydes conforming to formulas (VII), (VIII) or (IX) which are advantageously employed in the process of this invention include formaldehyde, acetaldehyde, propionaldehyde, butyraldehyde, isobutyraldehyde, n-valeric aldehyde, pival aldehyde, oenanthal, 2-ethylhexanal, hexahydrobenzaldehyde, benzaldehyde, p-chlorobenzaldehyde, p-nitrobenzaldehyde, $\beta$-methoxypropionaldehyde and $\beta$-ethoxypropionaldehyde.

Some examples of ketones conforming to formula (VII), (VIII) or (IX) which are advantageously employed in the process of this invention include acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone and cyclododecanone.

The percarboxylic acids of formula (VI) can be prepared according to known and conventional processes and employed either in the pure state if the nature of the particular acid so permits or in solution in a solvent which is inert with respect to the reaction medium, such solvents including, for example, water, ether, benzene, methylene chloride, dichloroethane, ethyl acetate. Or advantageously the peracids can be added to the reaction medium in the form of the crude solutions immediately following their preparation. Among the known and conventional processes for preparing the percarboxylic acids herein, the reaction of hydrogen peroxide with the chlorides or anhydrides of carboxylic acids or the carboxylic acid themselves and the autooxidation of aliphatic or aromatic aldehydes can be advantageously used.

The reaction components are reacted in the liquid phase and mixed in order or in various combinations. For example, the reaction components can be separately or simultaneously introduced into the reactor on a continuous or batch-wise basis. The percarboxylic acid can be added to a mixture of ammonia and the carbonyl compound or the ammonia or ammonia solution can be added to a mixture of the percarboxylic acid and the carbonyl compound if the latter is fairly stable with regard to the peracid and vice versa. It is advantageous to employ a solvent or blend of solvents to maintain a homogenous reaction medium. Examples of solvents which can be used for this purpose include the saturated alcohols having 1 to 6 carbon atoms such as methanol, ethanol, n-propanol, isopropanol, n-butanol, 2-butanol, isobutanol, tert-butanol, the amyl alcohols and cyclohexanol.

The temperature of the reaction can advantageously be from about 0° to 100°C. The reaction can be carried out at or below atmospheric pressure or at a pressure of up to 10 atmospheres if such is necessary to maintain the ammonia in solution.

The reaction components can be employed in stoichiometric quantities but it is also possible to use other proportions in which case, it is advantageous to react up to a ten-fold excess of ammonia and/or carbonyl compound by comparison to the amount of percarboxylic acid.

The calculation of the quantity of ammonia reacted is determined from the fact that a certain quantity of this reactant is required to neutralize the acidity of the percarboxylic acid or mixture containing the latter which quantity will vary according to the manner in which the mixture is prepared. This quantity of ammonia can be reduced or eliminated by a prior partial or total neutralization of the percarboxylic acid or its solution using another base, as for example, a hydroxide or carbonate of an alkaline or alkaline earth metal.

Moreover, the quantity of carbonyl compound employed in the reaction medium containing the peracid can be measured. Such can be the case when a solution of a peracid such as peracetic acid in acetone or in the crude product resulting from the autooxidation of an aldehyde, especially the mixtures containing acetaldehyde peracetate by the oxidation of acetaldehyde, are employed.

It can be advantageous to add one or more known and conventional stabilizers for percarboxylic acid or substances which exercise a buffering action on the pH of the reaction medium. For example, from about 0.1 to 1.0% by weight of the reaction medium of phosphoric acid, pyrophosphoric acid, nitrilotriacetic acid, ethylenediaminetetraacetic acid or the alkaline metal or ammonium salts of the aforesaid acids can be used. Upon completion of the reaction, the azines can be recovered from the medium by means of known and conventional techniques including extraction with a non-miscible solvent, fractional distillation or a combination of theses two methods.

The azines of this invention are useful as intermediates in the preparation of many important product and in particular are useful for preparing hydrazine and hydrazine salts by hydrolysis according to known and conventional methods. Hydrolysis of the azines releases the carbonyl compounds which can be recycled for preparing additional quantities of azines according to the method of this invention.

The following examples are illustrative of the method of this invention. Although the examples employ but a single carbonyl compound resulting in symmetrical azines it is understood that the same procedures can be followed except that two or more different aldehydes or ketones or one or more aldehydes and ketones are reacted to result in a mixture of symmetrical and unsymmetrical azines as hereinbefore described.

EXAMPLE 1

A solution of 8.1 gm ammonia (0.475 moles), 18 gm of acetone (0.31 moles), 10 gm water and 1 gm of the disodium salt of ethylene diaminetetraacetic acid in 160 gm of methanol were placed in a reactor and thereafter with the aid of a spatula over a period of 15 minutes, 18 gm of crystallized p-nitroperbenzoic acid (0.0935 moles) were added. The temperature of the reaction medium was held at 20°C during and after the addition of the acid while a light current of gaseous ammonia amounting to about 1.7 gm (0.1 moles) per hour was passed through the medium. After reacting for two hours, a sample of the reaction medium was withdrawn and the quantity of acetoneazine contained therein was determined by chemical analysis and controlled by gas phase chromatography. 5.5 gm (0.0495 moles) of acetoneazine corresponding to a yield of 53% by comparison to the total amount of the peracid were recovered.

The chemical analysis of the azine contained in the reaction medium was carried out by iodometry upon a sample wherein the amount of unconsumed peroxidic oxygen had been previously determined. A quantity of reaction medium was withdrawn containing approximately 2 milliequivalents of peroxidic oxygen which was precisely weighed and to which was added the following in this order: 12cm³ of a 30% by weight aqueous solution of sulfuric acid and 12cm³ of a 30% by weight aqueous solution of potassium iodide. The solution was left to stand away from the light for fifteen minutes after which the free iodine was titrated with a decinormal solution of sodium thiosulfate.

During this measurement of the peroxidic oxygen in the highly acid medium, the azine was quantitatively hydrolyzed to hydrazine sulfate which did not reduce the iodine under these conditions. Thereafter 50cm³ of an aqueous decinormal solution of iodine was added immediately followed by 30 gm of crystallized sodium acetate to give a pH near 5.0. Upon agitation, a release of nitrogen was observed which stopped after about two minutes and which proved that the iodine was reduced by the hydrazine according to the reaction

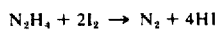

$$N_2H_4 + 2I_2 \rightarrow N_2 + 4HI$$

The excess iodine was then titrated using a decinormal solution of thiosulfate.

EXAMPLE 2

Potassium monopermaleate was prepared by introducing 86 gm of a 65% by weight solution of potassium hydroxide (1 mole) into a solution containing 98 gm maleic anhydride (1 mole) and 53.5 gm of a 70% by weight solution of hydrogen peroxide (1.1 moles) in 530cm³ of ethyl acetate at a temperature of 18°C. The mixture was maintained at this temperature for an hour after which the peroxygenated salt was filtered and dried at ambient temperature. The product thus obtained titrated 0.545 equivalents/100 gm of total peroxidic oxygen of which 0.456 was potassium monopermaleate and 0.089 unreacted hydrogen peroxide.

Over 30 minutes at 20°C., 17 gm of the crude peroxygenated salt (0.085 moles of potassium monopermaleate) were added to a solution of 6 gm ammonia (0.35 moles), 14.5 gm of acetone (0.25 moles), 4.5 gm of water and 0.25 gm of the disodium salt of ethylene diaminetetraacetic acid in 40 gm of methanol and the mixture was maintained at the same temperature while a light current of gaseous ammonia of about 0.1 moles/hour was passed therethrough. One hour after tthe addition was completed, the medium was titrated for acetoneazine. The quantity of acetoneazine determined by chemical analysis and controlled by gas phase chromatography was 0.5 gm (0.058 moles) corresponding to a yield of 68% by comparison to the total amount of potassium monopermaleate.

EXAMPLE 3

Monoperphthalic acid was prepared by introducing 60 gm of a 68% by weight solution of hydrogen peroxide (1.2 moles $H_2O_2$) into an agitated mixture of 148 gm of phthalic anhydride (1 mole) and 2 liters of 1,2-dichloroethane at 40°C and thereafter adding 5.23 gm of a 17% by weight aqueous solution of ammonia. After 10 minutes, the mixture was cooled to 20°C and the ammonia was neutralized with a stoichiometric amount of sulfuric acid. The mixture was left to react for another 30 minutes under agitation and the peracid titrated 0.508 equivalents per 100 gm of total peroxidic oxygen of which 0.375 were monoperphthalic acid and 0.133 were unreacted hydrogen peroxide.

20 gm (0.75 moles) of the crude peracid suspended in 18 gm of water were utilized. This suspension was added over 30 minutes at 20°C to a solution of 8.5 gm ammonia (0.5 moles) 14.5 gm of acetone (0.25 moles), 25 gm of water, .0125 gm of the disodium salt of ethylenediaminetetraacetic acid in 40 gm of methanol while about 0.1 mole/hour of nitrogen was being passed therethrough. 15 minutes after the addition was completed, the mixture was titrated. The amount of acetoneazine as determined by chemical analysis and controlled by gas phase chromatography was 7.1 gm (0.063 moles) corresponding to a yield of 84% by comparison with the total amount of monoperphthalic acid.

EXAMPLE 4

20 gm of the crude monoperphthalic acid (0.075 moles of the peracid) prepared in EXAMPLE 3 were suspended in 23 gm of water. This suspension was added over 30 minutes at 20°C to a solution of 8 gm of ammonia (0.47 moles), 18 gm of methylethylketone (0.25 moles), 25 gm of water and 0.25 gm of the disodium salt of ethylenediaminetetraacetic acid in 40 gm of methanol while causing a current of ammonia, about 0.1 moles/hour, to be passed therethrough. Fifteen minutes after this addition was completed, the reaction was titrated. The amount of methylethylketone azine determined by chemical analysis and controlled by gas phase chromatography was 8.5 gm (0.061 moles) corresponding to a yield of 81% by comparison with the total amount of monoperphthalic acid.

EXAMPLE 5

20 gm of the crude monoperphthalic acid (0.075 moles peracid) prepared in EXAMPLE 3 were suspended in 23 gm of water and the suspension was added to a solution of 8.5 gm of ammonia (0.5 moles), 24.5 gm of cyclohexanone (0.25 moles), 25 gm water and 0.25 gm of the disodium salt of ethylene diaminetetraacetic acid in 40 gm of methanol over a period of 30 minutes at 20°C while passing a light current of nitrogen, about 0.1 mole/hour, through the reaction medium. The mixture was left to react at this temperature for about 30 minutes and was then titrated by chemical analysis and gas phase chromatography. 5.7 gm of cyclohexanone azine (0.051 moles) had formed corresponding to a yield of about 68% by comparison to the total amount of peracid.

EXAMPLE 6

Performic acid was prepared in solution in an excess of formic acid by reacting 25.3 gm of formic acid (0.55 moles) and 5.3 gm of a 70% by weight solution of hydrogen peroxide (0.11 moles) for a half hour at 20°C followed by the addition of 0.25 g of concentrated sulfuric acid. Thereafter a mixture containing 0.10 moles of performic acid in a solution of 17 gm ammonia (1 mole), 18 gm acetone (0.31 moles), 13 gm of water and 0.5 gm of the disodium salt of ethylenediaminetetraacetic acid in 160 gm of methanol were added. This addition was carried out over 15 minutes at 20°C and the mixture was maintained at this temperature for 2 hours during which a current of 0.1 moles/hour of ammonia was passed through the mixture. Following analysis of the mixture, it was determined that 1.6 gm of acetoneazine (0.014 moles) corresponding to a yield of 14% by comparison to the total amount of peracid had formed.

EXAMPLE 7

A solution of peracetic acid was prepared by mixing 17.3 gm of glacial acetic acid (0.29 moles), 7.2 gm of a 68% by weight aqueous solution of hydrogen peroxide and 0.7 gm of concentrated sulfuric acid and reacting this mixture for several hours at ambient temperature. In this manner, a solution containing 0.10 moles of peracetic acid and 0.033 moles of unreacted hydrogen peroxide was obtained. This solution was added over a period of 30 minutes at 20°C to a solution of 8.5 gm ammonia (0.5 moles), 14.5 gm acetone (0.25 moles), 25 gm water and 0.25 gm of the disodium salt of ethylendiaminetetraacetic acid in 40 gm of methanol while at the same time passing a stream of gaseous ammonia, about 0.1 moles/hour, through the mixture. The mixture was left to react for fifteen minutes at this temperature and then titrated. 8.5 gm of acetoneazine (0.076 moles) corresponding to a yield of 76% by comparison to the total amount of peracid were found.

EXAMPLE 8

A 57% by weight aqueous solution of peracetic acid (0.10 moles) was added to a solution of 8.5 gm ammonia (0.5 moles) 14.5 gm of acetone (0.25 moles) and 0.25 gm of the disodium salt of ethylenediaminetetraacetic acid in 60 gm of water over a period of 30 minutes at 20°C. 8.1 gm of acetoneazine (0.072 moles) formed corresponding to a yield of 72% by comparison with the total amount of peracid.

EXAMPLE 9

A 24% by weight solution of peracetic acid (0.10 moles) in acetone (0.40 moles) was added to 57 gm of an aqueous solution of ammonia containing 15% ammonia by weight (0.5 moles) over 30 minutes at 20°C and left to react at this temperature for 30 minutes. 8.3 gm of acetoneazine (0.074 moles) formed corresponding to a yield of 74% by comparison with the total amount of peracid.

We claim:
1. A method for preparing azines which consists of reacting in the liquid phase
   a. ammonia;
   b. a carbonyl compound selected from formaldehyde, acetaldehyde, propionaldehyde, butyraldehyde, isobutyraldehyde, n-valeric aldehyde, pival aldehyde, oenanthal, 2-ethylhexanal, hexahydrobenzaldehyde, benzaldehyde, p-chlorobenzaldehyde, p-nitrobenzaldehyde, β-methoxypropionaldehyde, β-ethoxypropionaldehyde, acetone, 2-butanone, 2-pentanone, 3-pentanone, methyliso- propylketone, methylisobutylketone, methylcyclohexylketone, acetophenone, benzophenone, cyclobutanone, cyclopentanone, cyclohexanone, 2-methylcyclohexanone, 3-methylcyclohexanone, 4-methylcyclohexanone, 2,4-dimethylcyclohexanone, 3,3,5-trimethylcyclohexanone, cycloheptanone, cyclooctanone, cyclodecanone, and cyclododecanone, and mixtures thereof; and c. a percarboxylic acid selected from performic, peracetic, peroxypropionic, peroxybutyric, peroxyisobutyric, peroxyvaleric, peroxyisovaleric, peroxypivalic, peroxyhexanoic, peroxyheptanoic, peroxyoctanoic, α,α'-dimethylperoxyoctanoic, peroxylauric, peroxypalmitic, peroxystearic, hexahydroperoxybenzoic, trifluoroperacetic, β-chloroperoxypropionic, β-methoxyperoxypropionic, β-hydroxyperoxycaproic, peroxybenzoic and its chloro, bromo, fluoro, methoxy, nitro and trifluoromethyl derivatives, peroxytoluic, peroxysuccinic, peroxyglutaric, peroxyadipic, peroxycrotonic, peroxymaleic, peroxyfumaric and peroxyphthalic acid, and mixtures thereof, and recovering the azine or mixture of azines from the reaction medium.

2. The method of claim 1 wherein the reaction is carried out in the presence of a solvent comprising a saturated alcohol of from 1 to 6 carbon atoms.

3. The method of claim 1 wherein the reaction is carried out at a temperature between about 0° and 100°C.

4. The method of claim 1 wherein the molar ratios of carbonyl compound and/or ammonia to percarboxylic acid (VI) is between about the stoichiometric ratio and a ten-fold excess.

5. The method of claim 1 wherein the percarboxylic acid possesses a chlorine, bromine, or fluorine atom or a nitro, hydroxy, alkoxy, carboxylic acid, carbamyl or nitrile group.

* * * * *